April 21, 1953 H. E. DREW Plant Pat. 1,181
BLUEBERRY PLANT
Filed Oct. 13, 1951
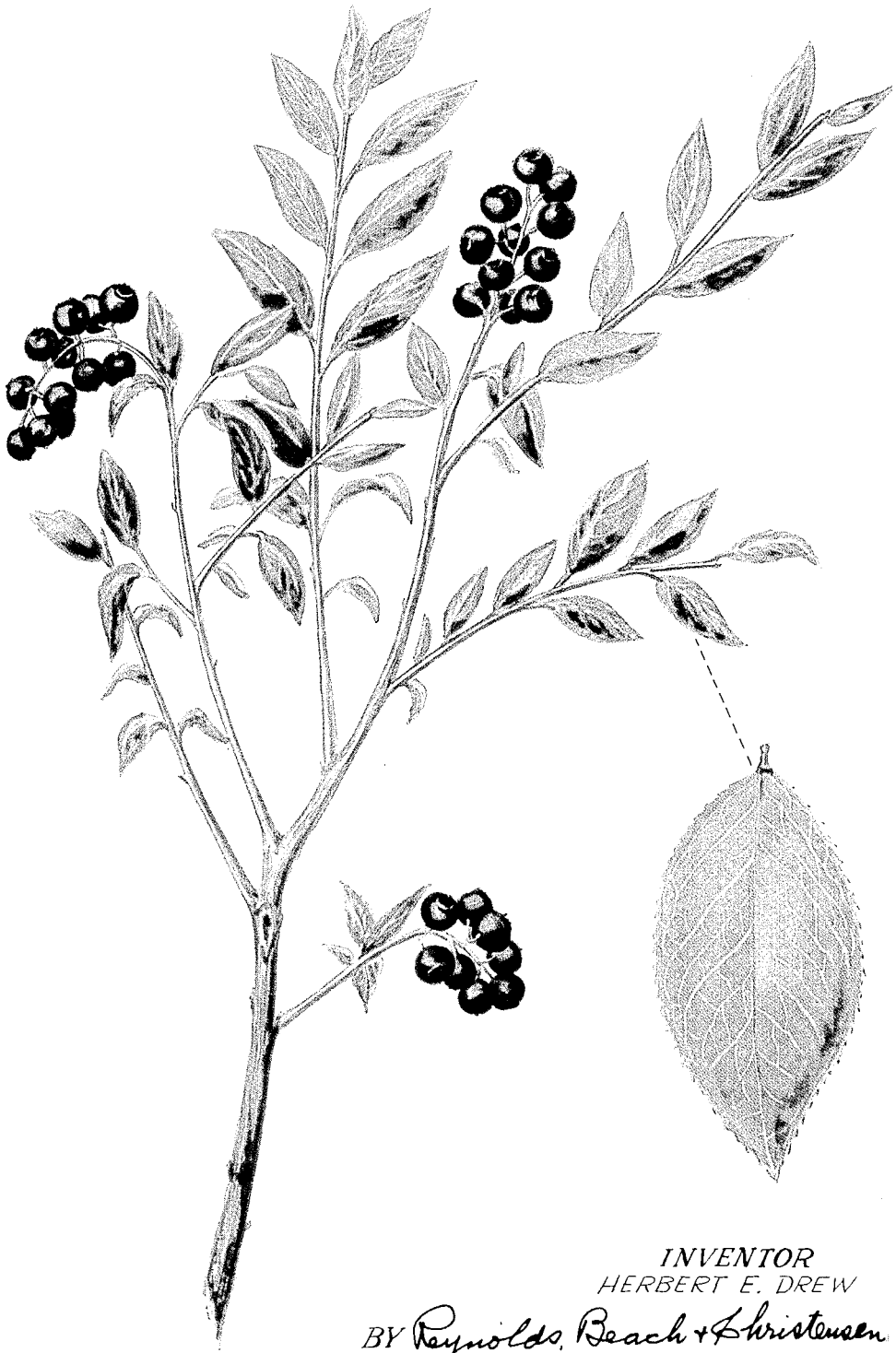
INVENTOR
HERBERT E. DREW
BY Reynolds, Beach & Christensen
ATTORNEYS Patented Apr. 21, 1953

Plant Pat. 1,181

UNITED STATES PATENT OFFICE 1,181

BLUEBERRY PLANT

Herbert E. Drew, Thurston County, Wash.; Alberta M. Drew, executrix of said Herbert E. Drew, deceased, assignor to herself individually Application October 13, 1951, Serial No. 251,173

1 Claim. (Cl. 47—62)

This invention relates to an improved blueberry plant, characterized primarily by the ripening of all berries on the bush virtually simultaneously, within a period of no more than a few days, wherefore all berries may be harvested at one picking, while possessing also desirable qualities suiting it for commercial production.

I raise almost all commercial varieties of blueberry on my farm in western Washington, on mineral soil, with irrigation, and hence am more familiar with the characteristics of the different varieties under the conditions prevalent there, than I am with their respective characteristics elsewhere and under different conditions. Where, hereinafter, a comparison is made with another variety, whether by way of distinction therefrom or of similarity thereto, the comparison refers to such varieties as grown by me under the conditions on my own farm. While the characteristics of the respective varities, including my new variety, will be generally the same in all blueberry-producing regions of the United States, it is probable that some variations will occur in one or in some characteristic when the new variety is grown in different regions, or under different soil, climatological, temperature, or other conditions; this probability is shown by like variations in characteristics of known varieties under different conditions. However, it is not expected that the distinguishing characteristics, hereinafter claimed, will differ, other than in minor degree.

All varieties of the cultivated highbush blueberry presently grown commercially, in all regions and under all conditions, mature their fruit over a sufficiently long period of time to require repeated pickings in order to remove the mature berries while they are at peak quality, and before they deteriorate on the bush, and in order to avoid admixture therewith of unripe berries and the economic loss of picking the unripe berries before they are mature, and of segregating picked immature berries from the mature. The number of pickings required will vary primarily with the variety; ordinarily at least three pickings will be required and in some instances five or more. Indeed, the Cabot variety, now generally discarded for that and other reasons, ripens over an especially long season, a matter of six or seven weeks, and requires sometimes as many as seven pickings, at intervals of five to seven days. Recognized commercial varities, such as Stanley, Rancocas, and Scammel, will require four to five pickings. The best I have been able to accomplish with June, which is distinguished by ripening all its fruit nearly at one time, is to ripen all its fruit within a period of two weeks, requiring at least three pickings.

The unripe fruit from high-bush blueberries must be left to mature, for maximum yield and quality, hence even though hand picking is not required for the purpose of preserving to the highest degree the quality of the individual berries—as it is in any event when they are destined for the fresh fruit market—hand picking has always been required heretofore even when the berries are intended for immediate processing, in order to avoid picking the unripe berries.

The virtually simultaneous ripening of all berries on my improved blueberry plant permits picking with a scoop or rake, which is the least expensive picking procedure, and avoids repetition of the picking, thereby greatly reducing harvesting expense, and enabling a much larger acreage to be harvested at the peak of the crop with no increase, but rather a decrease, in the total labor required in picking the same quantity of berries. At the same time the berries have and retain commercially desirable characteristics, so that there is no loss of value to balance or lessen the gain indicated. At the time of harvesting the entire crop is firm, crisp, fully ripe, and all in place on the bush, so that they are picked at the peak of their quality.

Another desirable characteristic of my improved blueberry plant is that the berries need not be picked as soon as they ripen, but can be left on the bush many days, even as much as two or more weeks, after ripening. They will remain full, firm, and crisp, and will not drop off. This enables a large field, coming ripe all at once, to be picked as labor is available, and to be harvested over a period of weeks, without loss of quality.

The Concord variety, although it has undesirable qualities that preclude its being grown extensively, is known to mature all its fruit quickly, and to hold it on the bush a long time. Held on the bush, it does not long retain its peak quality, is hard to pick, and does not keep well. All commercially grown varieties which are known to mature their berries in a short period of time, such as June, Concord or Weymouth (although none mature them so nearly simultaneously as my new blueberry) do not retain peak quality if those first to ripen are left on the bush any appreciable period of time—any such period, for example, as would reduce the number of pickings to one, or even in many cases to three, or two. My improved blueberry plant is not subject to these disadvantages.

With all its advantages, both those referred to above and those mentioned hereinafter, the fruit of my improved blueberry plant is quite favorably comparable in all respects to good commercial varieties. The detailed description will set forth in the characteristics of that fruit.

The annexed drawings, approximately three-quarter size, except for the detached individual leaf, which is approximately twice full size, and the following description, set forth the principal characteristics of my improved blueberry plant, apparent principally at harvest time.

My improved blueberry plant is a result of controlled cross-pollinization of the Rancocas and the June varieties. This was first done by me, at my own blueberry farm in western Washington, in the growing season of 1943. One of the resulting seedlings was selected as evidencing the desired qualities, and cuttings therefrom were set out in 1949; the two hundred rooted cuttings extant were permitted to come into bearing in 1952. The progeny, as well as the parent seedling, have now been observed through from one to six bearing seasons, and all have exhibited the distinguishing characteristics hereinbefore and hereinafter set forth in each of several widely different seasons. They have been subject to the longest dry spell recorded for the region, accompanied by unusually high temperatures; to an extremely wet season, and to the coldest winter on record for the region, with temperatures twice dropping to —6° F. Such varied climatic conditions appeared to have no effect upon the parent plant nor upon the progeny. All are growing, at my ranch, on mineral soil, with furrow or gravity irrigation.

Parentage, Rancocas×June. Bush erect, vigorous, branching habit—a rather unique characteristic—comparable to Rancocas; heavy producer. Leaf medium-sized, serrate, semi-glossy to glossy. Fruit cluster medium sized, medium loose. Berry medium sized, oblate, dark blue color, firm, crisp, slight aroma; the skin coloration tends to permeate the meat of the berry, giving it a bluish tinge when mature; medium in dessert quality. Scar, medium good. Ripens in early mid-season, and, as the principal distinguishing characteristic, berries ripen all virtually simultaneously—within two or three days—on the bush, and also remain in firm, crisp condition upon the bush through an unusually long period, such as two weeks or more on mineral soil, in western Washington. Not yet grown in any area other than western Washington. Regarded primarily as a processor berry, due to the fact that all can be picked at one time, thus reducing harvesting cost. The nature of the berry permits all clusters to be either hand-picked or scooped at one harvesting. Under winter conditions which produced winter injury to Wareham, Jersey and Scammell varieties, no winter injury to my new variety was observed. No susceptibility to disease has been observed.

My new variety is most nearly comparable to Rancocas in the bush and especially in its branching habit, in its leaf, the size and shape of the berry, its firmness, crispness, and dessert quality. It departs markedly from Rancocas, and from all other varieties known to me, in its habit of ripening all at one time, and in remaining at peak of quality on the bush over a long period of time, and also in resisting dropping if not picked promptly after it is ripe. The color of the berry is slightly darker than Rancocas, and the clusters are somewhat looser. Like Rancocas, it ripens in early midsetson, although a few days earlier than Rancocas first ripens. Also like Rancocas, or even superior thereto, it appears quite resistant to cold.

None of the named varieties of blueberry referred to in the specification are patented varieties.

I claim:

The new and distinct variety of blueberry plant as described, resembling most closely the Rancocas variety in the physical characteristics of the plant, leaf, and fruit, but characterized by the virtually simultaneous ripening of all berries on the bush, and the retention of all fruits in prime condition after ripening for a period approaching two weeks.

HERBERT E. DREW.

No references cited.